United States Patent [19]

Chodnekar et al.

[11] 4,027,033
[45] May 31, 1977

[54] PESTICIDES

[75] Inventors: Madhukar Subraya Chodnekar, Seltisberg; Peter Loeliger, Munchenstein; Ulrich Schwieter, Reinach; Albert Pfiffner, Bulach; Milos Suchy; Rene Zurfluh, both of Pfaffhausen, all of Switzerland

[73] Assignee: Hoffmann-La Roche Inc., Nutley, N.J.

[22] Filed: Mar. 3, 1976

[21] Appl. No.: 663,386

[30] Foreign Application Priority Data

Mar. 18, 1975 Switzerland .................. 3421/75
Dec. 22, 1975 Switzerland .................. 16586/75

[52] U.S. Cl. .................. 424/282; 260/340.5
[51] Int. Cl.² .................. A61K 31/36; C07D 317/44
[58] Field of Search .................. 260/340.5 R; 424/282

[56] References Cited
UNITED STATES PATENTS 3,948,952  4/1976  Gates et al. .................. 260/340.5

FOREIGN PATENTS OR APPLICATIONS 1,220,056  1/1971  United Kingdom ........ 260/340.5 R Primary Examiner—Ethel G. Love
Attorney, Agent, or Firm—Samuel L. Welt; Bernard S. Leon; Gerald S. Rosen

[57] ABSTRACT

Compounds represented by the formula

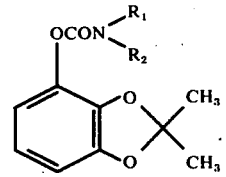

wherein
  $R_1$ is hydrogen or lower alkyl containing 1–4 carbons and
  $R_2$ is a halo-lower alkanoyl or dihalo-lower alkanoyl, said lower alkanoyls each containing 2–6 carbons useful as pesticides are disclosed.

11 Claims, No Drawings

PESTICIDES

DESCRIPTION OF THE INVENTION

The present invention relates to phenylcarbamates, a process for the manufacture thereof and pesticidal compositions containing same. The invention is also concerned with a method for the control of pests using as the active compound said phenylcarbamates.

The phenylcarbamate compounds provided by the present invention are represented by the following formula

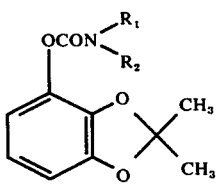   I wherein
  R₁ is hydrogen or lower alkyl containing 1–4 carbons and
  R₂ is a halo-lower alkanoyl or dihalo-lower alkanoyl, said lower alkanoyls each containing 2–6 carbons.

The compounds within the scope of formula I are useful as pest-control agents and are especially suitable for the control of insects.

According to the process provided by the present invention, the compounds within the scope of formula I are manufactured either by (a) reacting, in the presence of a base 2,2-dimethyl-4-hydroxy-1,3-benzodioxol represented by the formula

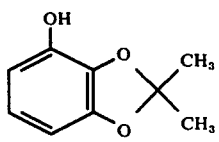   II with a compound represented by the formula

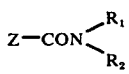   III wherein
  Z is chlorine, bromine or iodine and R₁ and R₂ have the same significance as in formula I, or by (b) reacting a compound represented by the formula

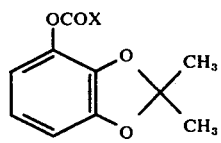   IV wherein X is chlorine, bromine or iodine,
with an amide represented by the formula

   V wherein R₁ and R₂ have the same significance as in formula I or by (c) reacting in the presence of a base a compound represented by formula

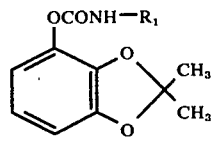   VI wherein R₁ has the same significance as in formula I with a compound represented by the formula

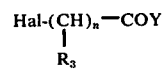   VII wherein Hal is halogen, R₃ is hydrogen or halogen, Y is chlorine, bromine or iodine and n is an integer of from 1 to 5.

As used in this specification, the term lower alkyl includes not only straight-chain but also branched-chain hydrocarbon groups containing 1–4 carbon atoms such as methyl, ethyl, propyl, isopropyl and the like. The term halogen includes the four halogen atoms fluorine, chlorine, bromine and iodine. The terms halo-lower alkanoyl and dihalo-lower alkanoyl include straight-chain and branched-chain alkanoyl groups containing 2–6 carbon atoms which are substituted with one or two halogen atoms, preferably chlorine, on any position in the alkyl group such as, for example, a haloacetyl, dihaloacetyl, halopropionyl, dihalopropionyl, halobutyryl or dihalobutyryl group. Preferred are chloroacetyl and n-chlorobutyryl, the chlorine being linked with the terminal methyl group.

Preferred compounds within the scope of formula I are those in which R₁ is methyl and R₂ is haloacetyl, preferably chloroacetyl or 4-chloro-n-butyryl.

Especially preferred compounds within the scope of formula I are 2,2-dimethyl-1,3-benzodioxol-4-yl-(chloroacetyl)-methylcarbamate and 2,2-dimethyl-1,3-benzodioxol-4-yl-(4-chlorobutyryl)-methylcarbamate.

According to embodiment a) of the process, the reaction of 2,2-dimethyl-4-hydroxy-1,3-benzodioxol with a compound of formula III is carried out conveniently in the presence of an excess of said compound of formula III. The reaction is conveniently carried out in an inert organic solvent such as a hydrocarbon, e.g., benzene or toluene, a chlorinated hydrocarbon, e.g., methylene chloride, an ether, e.g., diethyl ether and the like. As that catalyst there can be used a base such as potassium carbonate, sodium carbonate, triethylamine, pyridine and the like. The temperature and pressure are not critical; the reaction is preferably carried out at a temperature between about 0° C. and the reflux temperature of the reaction mixture, preferably at a temperature between room temperature and 130° C.

According to embodiment b) of the present process, a compound of formula IV is reacted with an amide of formula V. This reaction is carried out in an inert solvent such as, for example, an ether, preferably diethyl ether, dimethylformamide, a chlorinated hydrocarbon, preferably methylene chloride or chloroform; dimethyl sulphoxide or benzene. The reaction is advantageously carried out at a temperature between 0° C. and the boiling point of the reaction mixture. It is especially preferred to carry out the reaction at a temperature between 15° and 40° C. The pressure is not critical; the reaction is preferably carried out in an open vessel. The working-up of the reaction mixture is carried out by removal of the solvent and recrystallization of the resulting residue by conventional means.

According to embodiment c) of the present process, a compound of formula IV is reacted with a halo-lower alkane carboxylic acid halide or dihalo-lower alkane carboxylic acid halide. Examples of such acid halides are chloroacetyl chloride, dichloroacetyl chloride, 4-chlorobutyric acid chloride and the like. The reaction conditions are not critical and can be readily chosen. For example, the reaction can be carried out at room temperature or at a temperature above or below room temperature, in each case depending on the selected reagent. A preferred temperature range lies between room temperature and 130° C. Moreover, the reaction is conveniently carried out in a conventional inert organic solvent such as a hydrocarbon, e.g., benzene, toluene and the like, a chlorinated hydrocarbon, e.g., methylene chloride and the like, an ether, e.g., tetrahydrofuran and the like; dimethylformamide, pyridine and the like.

The starting materials used in the process provided by the present invention are either known or can be prepared in an analogous manner to the known compounds.

Pesticidal compositions of this invention contain as the essential active ingredient, one or more of the phenylcarbamates of formula I in association with a compatible carrier material. The pesticidal compositions conveniently contain at least one of the following substances: carrier materials, wetting agents, inert diluents and solvents.

The present invention is also concerned with a method for freeing from attack a locus subject to or subjected to attack by pests. The method comprises applying to said locus an effective amount of a pesticidal composition or of one or more of the phenylcarbamates of formula I. Thus, for example, the phenylcarbamates of formula I can be used for the control of pests on plants and animals and in the soil as well as on objects and areas.

The compounds within the scope of formula I are generally quite of value as pesticides. They are especially valuable as insecticides, especially against flies, caterpillars, beetles, aphids and Hemiptera. The compounds of this invention act as contact insecticides and, to some extent, also have systemic activity. The active compounds of this invention are also of value for the control of pests in animals. Thus, for example, 2,2-dimethyl-1,3-benzodioxol-4-yl-(chloroacetyl)-methylcarbamate in a concentration of $10^{-7}$g/cm$^2$ shows an activity of 100% in the test against *Carpocapsa pomonella* in the fifth larval stage and an activity of 90% in the test against *Musca domestica*.

The compounds within the scope of formula I are, in general, water-insoluble and can be made into a ready-for-use form by conventional means applicable to insoluble compounds.

When desired, the compounds of this invention can be dissolved in water-immiscible solvent such as, for example, a high-boiling hydrocarbon, which conveniently contains dissolved emulsifiers, so that it acts as a self-emulsifiable oil upon addition to water.

The active compounds can also be mixed with a wetting agent, with or without an inert diluent, to form a wettable powder which is soluble or dispersible in water. They also can be mixed with inert diluents to form a solid or pulverous product.

Inert diluents with which the active compounds of this invention can be processed are solid, inert materials, including pulverous or finely divided solid materials which as, for example, clays, sands, talc, mica, fertilizers and the like. The resulting compositions can be present either in the form of dusts or as materials having a larger particle size.

The wetting agent can be an anionic, cationic or non-ionic compound. Typical suitable anionic compounds are, for example, soaps, fatty sulfate esters such as dodecyl sodium sulfate, octadecyl sodium sulfate and cetyl sodium sulfate, fatty-aromatic sulfonates such as alkylbenzene sulfonates or butylnaphthalene sulfonates, complex fatty sulfonates such as the amide condensation product of oleic acid and N-methyl-taurin or the sodium sulfate of dioctylsuccinate.

Typical suitable non-ionic wetting agents, for example, condensation products of fatty acids, fatty alcohols or fat-substituted phenols with ethylene oxide, or fatty acid esters and ethers of sugars or polyvalent alcohols or the products which are obtained from the latter by condensation with ethylene oxide, or the products which are known as block copolymers of ethylene oxide and propylene oxide.

A typical suitable cationic agent is, for example, cetyltrimethylammonium bromide and the like.

The pesticidal compositions can also be present in the form of an aerosol. The aerosol composition can contain in addition to the propellant gas, which is suitably a polyhalogenated alkane such as dichlorodifluoromethane, as co-solvent and a wetting agent.

The pesticidal compositions provided by the present invention can contain, in addition to one or more of the active compounds of this invention, other active insecticides, bactericides and fungicides.

In their various fields of application, the compounds of this invention can be used in different ratios. Thus, for example, for the treatment of plants for the control of pests thereon, are conveniently used in an amount of about 10–1000 g/ha and for the treatment of animals for the control of ectoparasites thereon, the animal is conveniently dipped in a solution containing 10–500 parts per million of active compound, or sprayed with such a solution.

The following Examples illustrate the invention.

EXAMPLE 1

11.2 G. of 2,2-dimethyl-1,3-benzodioxol-4-yl-methylcarbamate are dissolved in 100 ml. of toluene and treated with 11.3 g. of chloroacetyl chloride. The resulting mixture is heated to reflux for 50 hours and then evaporated to dryness. The residue which forms is dissolved in a small amount of ether and treated with low-boiling petroleum ether until turbidity commences, whereby 1.6 g. of starting material can be recovered. The mother liquor is again evaporated to dryness and the resulting residue chromatographed over silica gel using methylene chloride for the elution to yield 2,2-dimethyl-1,3-benzodioxol-4-yl-(chloroacetyl)-methylcarbamate; $n_D^{25} = 1.518$.

EXAMPLE 2

11.2 G. of 2,2-dimethyl-1,3-benzodioxol-4-yl-methylcarbamate are dissolved in 100 ml. of toluene and treated with 14.7 g. of dichloroacetyl chloride. The resulting mixture is heated to reflux for 30 hours and then evaporated to dryness. The residue which forms is chromatographed over silica gel using methylene chloride for the elution to yield 2,2-dimethyl-1,3-benzodioxol-4-yl-(dichloroacetyl)-methylcarbamate of melting point 115°–116° C.

EXAMPLE 3

93 G. of 2,3-(isopropylidenedioxy)-phenyl-methylcarbamate is heated to boiling in 883 ml. of xylene and 117.5 g. of 4-chlorobutyric acid chloride. A strong stream of nitrogen is conducted through the solution in order to expel the liberated hydrogen chloride. After 40 hours, starting material can no longer be detected by means of a thin-layer chromatogram. The resulting clear brown solution is then evaporated on a rotary evaporator at 70° C./112 mm. and the residual brown oil is crystallized from alcohol in the cold to yield 2,2-dimethyl-1,3-benzodioxol-4-yl-(4-chlorobutyryl)-methylcarbamate of melting point 61°–62° C.

EXAMPLE 4

Spray Powder

A spray powder is made containing
50% active ingredient,
5% high-dispersible silicic acid,
1% sodium lauryl sulfate,
2% sodium lignosulfonate (sulfate cellulose spent liquor) and
42% kaolin.

The foregoing components are mixed and finely ground in a suitable mill. For the production of a finished spray solution, the powder is stirred into the desired amount of water.

We claim:

1. A compound represented by the

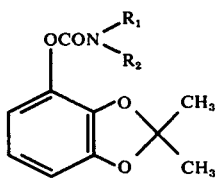

wherein
  $R_1$ is hydrogen or lower alkyl containing 1–4 carbon atoms and
  $R_2$ is halo-lower alkanoyl or dihalo-lower alkanoyl, said lower alkanoyls each containing 2–6 carbon atoms.

2. A compound of claim 1, wherein $R_1$ is hydrogen or lower alkyl containing 1–4 carbon atoms and $R_2$ is haloacetyl or dihaloacetyl.

3. A compound of claim 1 which is 2,2-dimethyl-1,3-benzodioxol-4-yl-(chloroacetyl)-methylcarbamate.

4. A compound of claim 1 which is 2,2-dimethyl-1,3-benzodioxol-4-yl-(dichloroacetyl)-methylcarbamate.

5. A compound of claim 1 which is 2,2-dimethyl-1,3-benzodioxol-4-yl-(chlorobutyryl)-methylcarbamate.

6. A pesticidal composition containing as the essential active ingredient a pesticidally effective amount of one or more compound of claim 1 in association with a compatible carrier material.

7. A pesticidal composition containing as the essential active ingredient a pesticidally effective amount of one or more compound of claim 2 in association with a compatible carrier material.

8. A pesticidial composition according to claim 7 wherein said active ingredient is 2,2-dimethyl-1,3-benzodioxol-4-yl-(4-chloroacetyl)-methylcarbamate.

9. A pesticidal composition according to claim 7 wherein said active ingredient is 2,2-dimethyl-1,3-benzodioxol-4-yl-(dichloroacetyl)-methylcarbamate.

10. A pesticidal composition according to claim 6 wherein said active ingredient is 2,2-dimethyl-1,3-benzodioxol-4-yl-(4-chlorobutyryl)-methylcarbamate.

11. A method for providing a locus subject to or subjected to attack by pests free from such attack, which method comprises applying to said locus a pesticidally effective amount of a pesticidal composition of claim 6.

* * * * *